(12) United States Patent
Donlagic et al.

(10) Patent No.: US 8,477,296 B2
(45) Date of Patent: Jul. 2, 2013

(54) OPTO-ELECTRONIC SIGNAL PROCESSING METHODS, SYSTEMS, AND APPARATUS FOR OPTICAL SENSOR INTERROGATION

(75) Inventors: Denis Donlagic, Maribor (SI); Matej Njegovec, Topolsica (SI)

(73) Assignee: University of Maribor, Moribor (SI)

( * ) Notice: Subject to any disclaimer, the term of this patent is extended or adjusted under 35 U.S.C. 154(b) by 566 days.

(21) Appl. No.: 12/758,738

(22) Filed: Apr. 12, 2010

(65) Prior Publication Data

US 2011/0249973 A1 Oct. 13, 2011

(51) Int. Cl.
*G01N 21/00* (2006.01)

(52) U.S. Cl.
USPC .......................................... 356/73.1

(58) Field of Classification Search
None
See application file for complete search history.

(56) References Cited

U.S. PATENT DOCUMENTS

| | | | |
|---|---|---|---|
| 4,452,079 A | 6/1984 | Tiller | |
| 4,852,079 A | 7/1989 | Kinney et al. | |
| 4,926,428 A * | 5/1990 | Kajiyama et al. | 372/20 |
| 4,996,419 A * | 2/1991 | Morey | 250/227.18 |
| 5,329,353 A | 7/1994 | Ichimura et al. | |
| 5,410,404 A | 4/1995 | Kersey et al. | |
| 5,729,347 A | 3/1998 | So | |
| 5,825,792 A | 10/1998 | Villeneuve et al. | |
| 5,838,437 A * | 11/1998 | Miller et al. | 356/478 |
| 6,327,287 B1 * | 12/2001 | Kner et al. | 372/43.01 |
| 6,351,476 B2 * | 2/2002 | Kner et al. | 372/20 |
| 6,693,928 B2 * | 2/2004 | May | 372/19 |
| 6,980,297 B2 | 12/2005 | Maeda | |
| 7,027,473 B2 * | 4/2006 | Sasaki | 372/32 |
| 7,060,967 B2 | 6/2006 | Thingbo et al. | |
| 7,139,295 B2 * | 11/2006 | Tsai et al. | 372/20 |
| 7,157,693 B2 * | 1/2007 | Thingbo et al. | 250/227.18 |
| 8,351,473 B1 * | 1/2013 | Darcie et al. | 372/20 |
| 2002/0054408 A1 * | 5/2002 | Lee | 359/136 |
| 2007/0252998 A1 | 11/2007 | Berthold et al. | |
| 2007/0280703 A1 * | 12/2007 | Taverner et al. | 398/195 |
| 2009/0059209 A1 * | 3/2009 | Nguyen et al. | 356/73.1 |
| 2009/0251684 A1 * | 10/2009 | Arai et al. | 356/43 |
| 2011/0158269 A1 * | 6/2011 | Ono et al. | 372/29.02 |

FOREIGN PATENT DOCUMENTS

| | | | |
|---|---|---|---|
| JP | 2005147909 A | * | 6/2005 |
| JP | 2008046046 A | * | 2/2008 |
| WO | WO 2009/032947 | | 3/2009 |

OTHER PUBLICATIONS

Donlagic et al., U.S. Appl. No. 13/046,659, filed Mar. 11, 2001.
Donlagic et al., U.S. Appl. No. 13/046,648, filed Mar. 11, 2001.
Donlagic, U.S. Appl. No. 13/046,666, filed Mar. 11, 2001.

* cited by examiner

*Primary Examiner* — Gordon Stock, Jr.
(74) *Attorney, Agent, or Firm* — Dugan & Dugan, PC (57) ABSTRACT

Opto-electronic signal processing systems, apparatus and methods to extract a measured parameter from one or more interrogated optical sensors are disclosed. The apparatus includes an integrated laser module, an electronic control and processing unit, an optical coupling element, and one or more light receivers. Light is reflected back from the optical sensor through the optical coupling element to the light receiver(s). The electronic control and processing unit controls the wavelength of the integrated laser module using thermal control and, at the same time, detecting the wavelength of the integrated laser module using a wavelength selective element of the integrated laser module. According to the method, a wavelength sweep from the integrated laser module wavelength is swept, simultaneously measured and stored in memory of the electronic control and processing unit. The optical sensor response is recorded during the sweep and combined with stored emitted wavelengths to obtain spectral characteristics of interrogated optical sensor. Numerous other aspects are provided.

21 Claims, 8 Drawing Sheets

OPTO-ELECTRONIC SIGNAL PROCESSING METHODS, SYSTEMS, AND APPARATUS FOR OPTICAL SENSOR INTERROGATION

FIELD OF THE INVENTION

The present invention relates to methods, systems and apparatus adapted for testing optical devices such as optical sensors, and more particularly to methods, systems and apparatus to measure spectral characteristics of one or more optical sensors.

BACKGROUND OF THE INVENTION

Optical sensors (e.g., fiber optic sensors) are used in various applications due to their unique properties, such as small size, dielectric structure, electromagnetic immunity, robustness, chemical durability, high sensitivity, and cylindrical geometry. These properties make optical sensors especially suitable for applications in extreme environments, biomedical applications, and in all fields of industrial application. They may be used to measure almost any physical or chemical parameter such as strain, temperature, pressure, acceleration, refraction index, displacement, and others. Many optical sensors may be designed to change their spectral characteristics under the influence of a measured parameter. For example, a sensor may change a peak wavelength value within a reflected characteristic spectrum, when exposed to variations of the measured parameter. Such optical sensors may be, for example, fiber Bragg gratings or Fabry-Perot interferometer based sensors. The measured parameter (e.g., strain, temperature, pressure, acceleration, refraction index, displacement, and others) in these types of optical sensors may be extracted by acquisition, and the processing of their spectral characteristics.

Various systems and methods for interrogating optical sensors have been researched and described. Interrogation, as used herein in its broadest sense, means to determine one or more spectral characteristics of an optical sensor. However, prior systems generally require relatively complex electronic and optical subsystems to accomplish sensor interrogation. One of the most direct and commonly used systems for the determination of measured parameters from the spectral characteristics of fiber optic sensors is based on using a wide-band optical source of about 15 nm to 100 nm or more and an optical spectrum analyzer. Light generated by the wide-band optical source travels through an optical fiber to the optical sensor. The optical sensor then reflects back part of the optical spectrum, which is then captured by the optical spectrum analyzer. The optical spectrum analyzer acquires the spectral characteristics of the back-reflected light and searches for specific features within the spectral characteristics, such as peak wavelength within the back reflected optical spectrum, for example. This peak wavelength, thus, may provide information about a measured physical or chemical parameter, i.e., when the optical sensor is exposed to a physical or chemical input.

In general, the main disadvantage of systems employing spectral analysis is in the complex structure of the optical spectrum analyzer, especially when high resolution wavelength measurements are desired, which is the case in most practical optical sensor applications.

Somewhat simpler sensor interrogation systems may be built by application of narrow-band optical sources with a tunable wavelength. In one prior system, for example, measuring pressure using a Fabry-Perot interferometer, and temperature using a Bragg grating sensor, may be based on wavelength sweeping of a tunable laser source in combination with an optical time-domain reflectometer (OTDR). Short pulses of different wavelengths may be sent to the optical sensor. From time differences between the reflected signals, it may be possible to reconstruct the spectral characteristics of each individual optical sensor. However, such prior systems based on OTDR are generally complex, expensive, and inappropriate for interrogating small numbers of sensors.

Other prior art systems utilize wavelength control of a tunable optical source during wavelength sweeping. However, such tunable optical sources are complex elements. They can be made either from a broad-band optical source and tunable narrow-band filter or by using more complex technology such as laser sources with a wavelength tunable optical feedback, such as tunable optical resonator. Both versions can provide a widely tunable wavelength range of between about 10 nm and 300 nm. However, the complexities and associated high costs of such sources may only justify their application in systems containing a large number of sensors. Furthermore, the wavelength of the narrow-band tunable optical sources can drift with aging. This drift may cause long term instabilities. For this reason, these kinds of systems use an additional external wavelength reference for precise determination of optical source wavelength. Such references help in wavelength determination of an optical source, but they also exhibit temperature dependence, which may cause errors when measuring a physical parameter with the optical sensor. Of course, use of such reference units may limit the minimum size of the system, add reliability issues, and increase the complexity and cost of the system. Their use is thereby justified in larger and more complex sensor networks, while such an approach is generally inappropriate for a single sensor or signal interrogations with a low number of channels.

For the above-described reasons, there is a long felt and unmet need for highly integrated and compact optical sensor interrogation methods, systems, and apparatus.

SUMMARY OF THE INVENTION

In one aspect, an opto-electronic signal processing apparatus is provided. The apparatus includes an integrated laser module; a light receiver; an optical coupling element, having at least a first port, a second port and a third port, the first port of the optical coupling element being optically coupled to the integrated laser module, the second port of the optical coupling element being optically coupled to the light receiver, and the third port of the optical coupling element being optically coupleable to an optical sensor to be interrogated; and an electronic control and processing unit electrically coupled bi-directionally to the integrated laser module wherein the electronic control and processing unit is adapted to receive spectral characteristics of the optical sensor being interrogated based upon a wavelength sweep of emitted light signals sent by the integrated laser module reflected by the optical sensor and received by the light receiver, and simultaneously receiving from the integrated laser module a wavelength of light being emitted by the integrated laser module.

In another aspect, an optical sensor interrogation system is provided. The system includes an integrated laser module; a light receiver; an optical coupling element being optically coupled to the integrated laser module and optically coupled to an optical sensor to be interrogated; and an electronic control and processing unit electrically coupled bi-directionally to the integrated laser module wherein the electronic control and processing unit is adapted to receive spectral characteristics of the optical sensor based upon a wavelength sweep of emitted light signals sent by the integrated laser module, which are reflected by the optical sensor and received by the light receiver, and simultaneously receive a wavelength of emitted light from the integrated laser module.

In yet another aspect, a method of interrogating an optical sensor is provided. The method includes providing an optical sensor to be interrogated; generating a wavelength sweep of emitted light signals from a laser source of an integrated laser module through an optical coupling element to the optical sensor; reflecting the emitted light signals from the optical sensor thereby providing reflected light signals; passing the reflected light signals through the optical coupling element and receiving the reflected light signals at a light receiver; receiving at a electronic control and processing unit, signals corresponding to spectral characteristics of the optical sensor based upon the reflected light signals received by the light receiver; and substantially simultaneously receiving from the integrated laser module an instantaneous signal correlatable to an emitted light wavelength of the wavelength sweep being emitted by the integrated laser module.

Numerous other aspects are provided in accordance with these and other aspects of the invention. Other features and aspects of the present invention will become more fully apparent from the following detailed description, the appended claims, and the accompanying drawings.

DETAILED DESCRIPTION

According to embodiments of the invention, methods, systems and apparatus are provided for obtaining stable, repeatable, accurate, and fast interrogation of optical sensor spectral characteristics. The systems and apparatus are based upon a small number of common, cost-effective opto-electronic components. In particular, the apparatus and systems include an integrated laser module; a light receiver such as a photodetector; an optical coupling element being optically coupled to the integrated laser module and also optically coupled to an optical sensor to be interrogated; and an electronic control and processing unit electrically coupled bi-directionally to the integrated laser module. The electronic control and processing unit is adapted to receive spectral characteristics of the optical sensor based upon a wavelength sweep of emitted light signals sent from the integrated laser module. The emitted light signals are reflected by the optical sensor and received by a light receiver (e.g., a photodetector). Simultaneously, a signal indicative of a wavelength of emitted light from the integrated laser module is received by the electronic control and processing unit. Accordingly, an exacting correlation may be made between the reflected signals and the wavelength of the emitted light thereby allowing a precise determination of the spectral characteristics of the optical sensor.

As a result, the present invention may advantageously require very few opto-electronic and electrical components and devices thereby allowing for very compact, robust and cost effective apparatus and systems. Moreover, the present invention may be applicable in optical sensing applications where high resolution measurements are required. In some embodiments, a plurality of sensors may be interrogated with desired resolution and dynamic properties.

These and other embodiments of the present invention are further described with reference to FIGS. 1-14 below.

Figure 1:
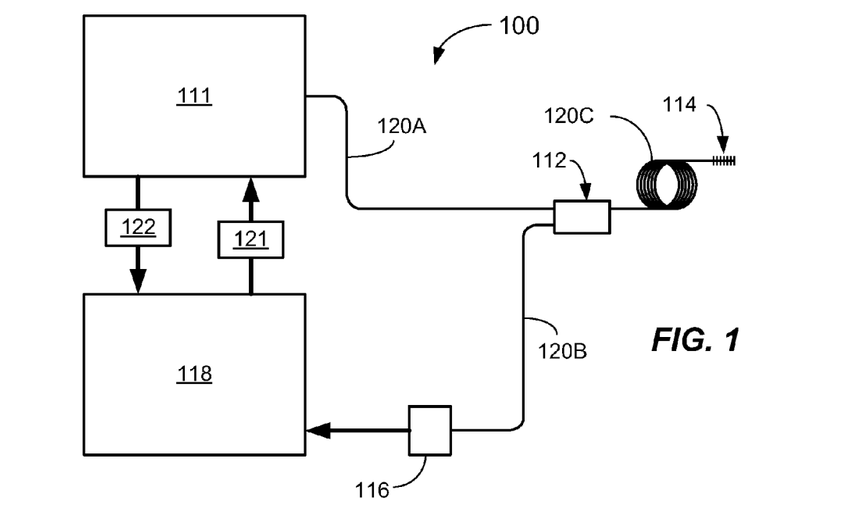
FIG. 1 is a schematic diagram of an opto-electronic signal processing apparatus according to embodiments of the invention.

A first embodiment of the present invention is described with reference to FIG. 1. An opto-electronic signal processing apparatus 100 of the present invention includes an integrated laser module 111, an optical coupling element 112, a light receiver 116 such as a photodetector, and an electronic control and processing unit 118. The apparatus 100 is optically coupleable to one or more optical sensors 114. The various optical components of the opto-electronic signal processing apparatus 100 are connected together with conventional optical fibers 120A, 120B and the optical sensor 114 may be optically coupled via a length of optical fiber 120C. The connections of the optical fibers 120A-120C to the various apparatus components and an optical sensor 114 may be made for example via optical connectors or by splicing of optical fibers.

In operation, light signals generated by the integrated laser module 111 may be output and travel to the optical sensor 114, which is adapted to be interrogated through a length of optical fiber 120A coupled to a laser source (more fully described below), an optical coupling element 112, and through a length of optical fiber 120C. The respective lengths of the fibers 120A, 120B may be of any suitable length, such as between 0.05 m and 2 m, for example. The length of optical fiber 120C may be between about 0.3 m and up to 360 km or more, for example. The optical fibers 120A-120C may be any suitable type of optical fiber, such as single mode fiber (e.g., SMF-28 type optical fiber available from Corning Incorporated of Corning, N.Y.). Other types and lengths of optical fiber may be used.

The light signal emitted from the integrated laser module 111 then reflects off from the optical sensor 114 and back to the optical coupling element 112, where it is diverted to a light receiver 116 (e.g., photodetector). The light receiver 116 produces electrical signals over time, which may be proportional to the reflected light signals received thereat. The light receiver 116 may be a photodetector made from InGaAs (commonly used for wavelengths of about 1550 nm or 1310 nm), or germanium or silicon (for a laser module that operates at wavelengths shorter than about 110 nm, for example). Other suitable types of light receivers (e.g., photosensors) may be used.

The electronic control and processing unit 118 functions to control and monitor the electrical signals generated by the integrated laser module 111, and also receives the electrical signals from the light receiver 116 (e.g., photodetector). These signals may be signals indicative of light reflected from the optical sensor 114 that is undergoing interrogation. The electronic control and processing unit 118 may control the integrated laser module 111 by controlling a wavelength of emitted light provided to interrogate the optical sensor 114. In addition, the electronic control and processing unit 118 may monitor signals indicative of the emitted wavelength from the integrated laser module 111 provided to the optical sensor 114. From this information, spectral characteristics of the interrogated sensor may be obtained. From the spectral characteristics, a specific feature of may be deciphered by known algorithms. For example, once the spectral characteristics of the sensor are obtained and stored into the memory of the electronic control and processing unit, a peak searching algorithm may be applied to find maximum or maxima in this characteristic. In optical sensors, such as fiber Bragg gratings, the wavelength corresponding to a maximum reflectivity can be directly correlated to the measured parameter. In sensors with periodic spectral characteristics such as Fabry-Perot sensors, a position of a particular maximum in spectral characteristics may be tracked, or distance between multiple peaks may be measured to determine the measured parameters. A peak searching algorithm may be realized in many ways, including but not limited to a simple scanning of all stored values for a maximum or peak value of reflectivity; interpolation of the scanned characteristic with a mathematical function, derivation of this mathematical function and solving its derivative for zero; and similar methods. It is however also possible to search for features other than peaks in the spectral characteristic, such as minima, periodic characteristics, a phase change in the wavelength domain, certain slope values of the spectral characteristics, or their derivates, number of peaks and/or minimums amplitudes within a specified wavelength range, and similar features. The spectral features of interest and procedures for their extractions will in generally depend on the interrogated sensor's construction and characteristics and can vary accordingly. From a change in the specific detected feature (e.g., a peak position shift), a measured parameter which is correlatable to the change, may be determined. The measured parameter of the optical sensor 114 may be a physical or chemical parameter, such as strain, temperature, pressure, acceleration, refraction index, displacements, chemical concentration and others, depending upon the type of optical sensor 114 being interrogated. Suitable electronic components 121, 122, which may be amplifiers, filters, A/D or D/A converters may be employed, as needed, to convert analog signals received from the integrated laser module 111 and light receiver(s) 116 to useable digital form, and likewise to convert digital control signals generated by the electronic control and processing unit 118 to analog signals useable by the components of the integrated laser module 111, if needed.

The electronic control and processing unit 118 may be any suitable digital signal processor, microcomputer, microcontroller, FPGA or personal computer including a suitable processor, which is capable of carrying out programmed instructions and or mathematical algorithms. In some instances, the electronic control and processing unit 118 may be integrated into the integrated laser module 111. The electronic control and processing unit 118 may include a suitable display for displaying the spectral characteristics of the interrogated sensor, and/or the measured result or optical feature of the optical sensor or sensors being interrogated. The electronic control and processing unit 118 may also carry out various algorithms for determining features of the spectral characteristics for each sensor (e.g., reflected intensity peaks) and for determining a measured parameter based on a change in the feature upon exposure to a physical or chemical parameter. The electronic control and processing unit 118 can be further adapted to perform other tasks, such as safety functions based on a measured parameter, such as alarming, or it can be included in closed loop control systems. The electronic control and processing unit 118 may have integrated modules for serial communication such as USB, UART, I2C, SPI, ECAN, etc. so connection with other devices is relatively simple.

The optical coupling element 112 may be any suitable element functioning to allow light signals to pass in one direction and to divert reflected light signals traveling in an opposite direction. For example, the optical coupling element 112 may be an optical coupler, an optical circulator, a beam splitter, or a similar functioning device. An optical fiber coupler may be used in many applications due to its simplicity and low cost. Other types of optical coupling elements may be employed.

Figure 2:
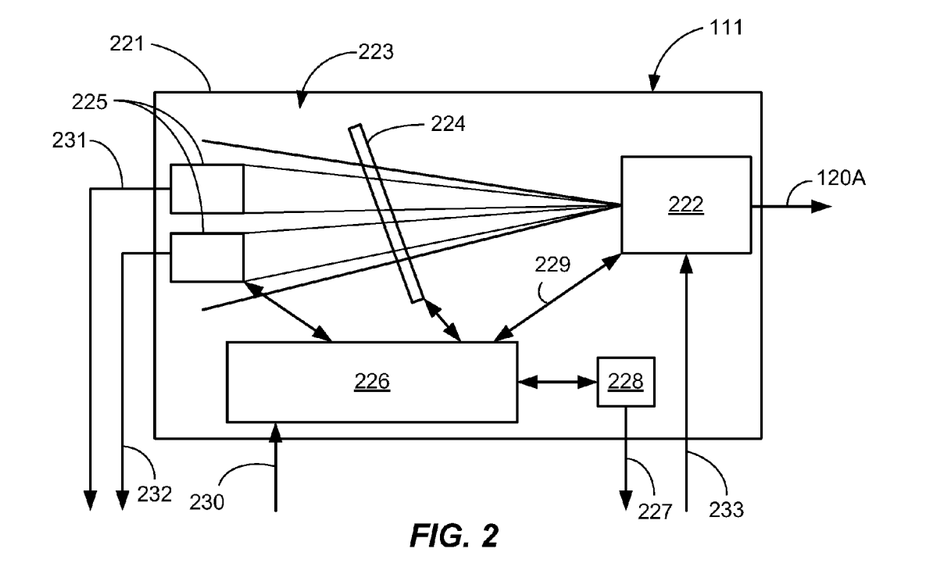
FIG. 2 depicts an exemplary embodiment of an internal structure of an integrated laser module according to the prior art.

In the present invention, the integrated laser module 111 may be a compact, integrated, opto-electronic device of the type used for telecom applications. The integrated laser module 111 is an integrated component and includes, as shown in FIG. 2, a housing 221 containing a laser source 222, such as a laser diode, a wavelength measurement apparatus 223, and one or more elements for thermal control of at least the laser source, such as thermoelectric cooler 226 and temperature sensor 228. Such integrated laser modules 111 are widely available commercially, frequently used in telecom applications, and thus, may be relatively cost effective devices. However, such integrated laser modules are generally used as constant and stable wavelength sources. Such integrated laser modules are, for example, described in U.S. Pat. No. 5,825,792 and U.S. Pat. No. 7,027,473, the disclosures of each of which are hereby incorporated by reference herein.

Again referring to FIG. 2, an internal design for an embodiment of integrated laser module 111 is depicted. The integrated laser module 111 includes a housing 221 which contains the various module components. The subcomponents include a laser source 222, a wavelength measurement apparatus 223, and at least one element for thermal control of at least the laser source 222, such as a thermoelectric cooler 226. A temperature sensor 228 may be employed to provide a temperature feedback signal, which may be measured against a desired set point, for example. The signal indicative of measured temperature may be an analog signal provided to the electronic control and processing unit 118 via signal line 227.

The laser source 222 may be any suitable laser source, such as a laser diode. The laser source 222 may be operated continuously or in a pulsed mode, for example. In some embodiments, a distributed feedback (DFB) laser may be used. In place of the DFB laser diode, it is also possible to use any other narrow band laser diode, such as a distributed back reflector (DBR) laser diode, a Fabry-Perot laser diode, a vertical cavity surface-emitting laser (VCSEL) diode, or the like. Other types of laser diodes may also be used as the laser source 222. The laser source 222 may have an output power typically between about 0.5 mW to about 15 mW, or even up to about 0.5 W, for example. Laser sources having more or less power may be used. The laser source 222 (e.g., laser diode) within the integrated laser module 111 may be a narrow-band optical source, and is generally considered as a source with a fixed wavelength output. The output wavelength of the laser source 222 may, however, be changed within a very limited range of wavelengths. This wavelength adjustability may be accomplished by using an inherent temperature dependency of the laser source, and/or by controlling a drive electrical current to the laser source 222, as will be described below.

In the case where the temperature dependence is used to accomplish a change in an emitted wavelength of the laser source 222, the wavelength of the laser source 222 may be adjusted between wavelength limits based upon changing a temperature exposure, and thus a nominal temperature, of the laser source 222. This may be accomplished by exposing the laser source 222 to relative heating or cooling via the thermoelectric cooler 226. However, any suitable heating and/or cooling device may be used. For example, heating may raise the emitted wavelength whereas cooling may lower the emitted wavelength of the laser source 222. This may provide an approximate wavelength adjustment band of between about 0.8 nm and 4 nm by using the inherent temperature dependence of the laser source 222. A slow sweep using inherent temperature dependence may be accomplished at a rate of between about 0.001 Hz and 1 Hz, for example.

When employing drive current to accomplish a change in an emitted wavelength of light from the laser source 222, an electrical current provided to the laser source 222 is modulated. This modulation may result in an approximate range of wavelength adjustment between about 0.15 nm and 1 nm, for example. Other wavelength adjustment ranges, which are smaller than the range due to the temperature dependency of the laser source, may be used. In some embodiments, a combination of the temperature dependence of the laser source 222 together with controlling a drive electrical current to the laser source 222 may be utilized. Using the temperature dependence results in a slowly changing process, but may result in sufficiently broad sweeps to enable sensor interrogation of detectable features in the spectral characteristics. Using current sweeps may be performed at rates which are relatively quicker than using the temperature dependence. For example, the fast sweeps between a minimum frequency and maximum frequency may be accomplished at a rate of between about 1 Hz to 10 KHz or even higher. Other rates for the fast sweeps may be used. Temperature is therefore used for wider but slow sweeps, and current is used for shorter and faster sweeps. Furthermore, the temperature may be used to make adjustments to keep the fast sweep capability within its range.

For example, in some embodiments, the combination of both may be used. For example, the temperature dependence may be first used to perform a slow sweep, which is used to identify a desired spectral feature. The temperature dependence is then again used to set a wavelength of the laser source 222 near (e.g., just below) a wavelength of the desired spectral feature of an optical sensor. Then the sweep may be accomplished at a faster rate, and over a narrower sub-range, using the drive current of the laser source 222 to more accurately determine the location or characteristic of the desired spectral feature.

The wavelength measurement apparatus 223 may be any suitable component integrated within the integrated laser module 111, which may provide a signal indicative of, or which may be correlated to, the emitted wavelength of the laser source 222. In some embodiments, the wavelength measurement apparatus 223 may include a wavelength selective element 224 and one or more light intensity measuring sensors (e.g., photodetectors 225). In the depicted embodiment, a pair of light intensity measuring sensors (e.g., photodetectors 225) are employed. The wavelength selective element 224 may be a Fabry-Perot filter (e.g. etalon). The wavelength selective element 224 may have a transmission spectrum, which functions to divide a portion of the emitted light from the laser source 222 into a series of fringes or peaks spaced in wavelength and including a free spectral range (FSR). The width of the transmission peaks are reduced based upon the finesse of the etalons. Fines of the etalon may be set by their production process in order to provide or cover a desired wavelength range of interest. Lower fines which may yield a nearly continuous and nearly liner characteristics within certain wavelength range may be preferentially used. Other types of Etalons may be used.

Optical fiber 120A is often coupled directly to laser source 222 (e.g., laser diode) by way of butt coupling, for example. For example, the laser diode's active surface is small enough to be aligned with optical fiber's core or through the use of a collimating and focusing lens assembly coupled to the laser source 222. In many cases this coupling is accomplished through an optical isolator coupled between the laser source 222 and the optical fiber 120A to eliminate potential back reflections. The wavelength measurement apparatus 223 including the wavelength selective element 224 and photodetectors 225 may function as a reference for determining a precise value of an output emitted wavelength of the laser source 222. The reference signals generated by the intensity-measuring photodetectors 225 may be provided to the electronic control and processing unit 118 in signal lines 231, 232. From these intensity signals, an exact operating wavelength of the emitted light signals may be determined, which will be described more thoroughly below. Wavelength selective element and detectors provided in the form of a wavelength locker are well known for use in telecom systems to achieve and lock a constant wavelength output of the DWDM laser module.

As described above, a temperature of the laser source 222 may be controlled to adjust the emitted wavelength of the laser source 222 by providing an electrical current through the thermoelectric cooler 226 in signal line 230, which may be thermally coupled to at least the laser source 222. The thermal coupling may be by conductive, convective, and/or radiative coupling. For example, the laser source 222 may be in direct thermal conductive contact with a temperature changeable portion of the thermoelectric cooler 226 as indicated by arrow 229. The temperature of the laser source 222 may be controlled by the electronic control and processing unit 118 to a desired set point, for example. Feedback regarding the set point temperature may be provided to the electronic control and processing unit 118 by the temperature sensor 228 in signal line 227. Accordingly, it should be recognized that the desired set point may be commanded and controlled via an electrical signal from the processing and control unit 118 in signal line 230, and feedback may be provided from the temperature sensor 228 in signal line 227. Accordingly, changes in an operating temperature of the laser source 222 may be used to accomplish a change in the emitted wavelength of the laser source 222. The thermoelectric cooler 226 may be thermally coupled to one or more of the other components of the integrated laser module 111, as well, as indicated by the double ended arrows.

Typically, all of the optical and electronic elements of the integrated laser module 111 may be thermally coupled to the thermoelectric cooler 226, which allows complete or nearly complete elimination of environmental temperature effects when determining the output wavelength of the laser source 222. The entire integrated laser module 111 may be packaged in a common and compact housing 221, and may have a total volume less of than about three cubic centimeters, for example.

This type of integrated laser module 111 is usually used in dense wavelength division multiplexing (DWDM) telecommunication systems. This type of integrated laser module 111 is typically used to cover a specific channel of DWDM system. Other types of integrated laser modules 111 can also cover more than one channel, and may, thus, be tuned to emit a constant wavelength over a somewhat wider range of wavelengths. This particular type of integrated laser module 111 is designed to provide light with constant wavelength, but can be tuned to more than one channel within dense wavelength division multiplexing (DWDM) telecommunication systems. However, these kinds of integrated laser modules for DWDM are not typically designed for wavelength sweeping, but are operated to provide a defined, steady wavelength output locked at a single output wavelength.

The inventors herein have utilized the natural wavelength sensitivity of the laser source 222 of the integrated laser module 111 to temperature and/or electrical drive current to the laser source 222 to cover a wavelength span (see span above). This relatively narrow wavelength range is sufficient to interrogate certain types of optical sensors 114. In other examples, drive current to the laser source 222 may be modulated by controlling an electrical current in signal line 233 to the laser source 222. The drive current affects emission wavelength through carrier density change in the active region of the laser diode. This leads to refractive index change of the laser resonator. Another reason can be found in localized thermal effects that cause heating of the resonator and thereby its refractive index change. In both cases, the emission wavelength is changed due to the change in resonator characteristics. The emission wavelength dependency on the laser diode drive current is well known and in telecommunication systems generally considered an undesired phenomenon.

For example, a typical wavelength sensitivity of a DFB laser diode to temperature is approximately 0.08 nm/° C. Similarly, a typical wavelength sensitivity of a DFB laser diode to the drive current usually lies within the 5 to 10 pm/mA range. Thus, spectral characteristics of the optical sensor 114 may be interrogated by a wavelength sweep of the integrated laser module 111 across a relatively narrow wavelength band (see above) by utilizing this temperature sensitivity, drive current, or both in combination. A combination of changing both a temperature and drive current of the laser source 222 may be used to improve a dynamic property of the interrogation of the optical sensor 114. For example, the temperature sweep may be relatively slow, but may cover a relatively wider band of wavelengths. The current sweep may be relatively fast, but can only cover a relatively narrower band of wavelengths.

In operation, such temperature and/or drive current modulation may cause relatively strong output optical power swings (variations) from the integrated laser module 111. Therefore, the optical power recorded by the light receiver 116 depends on the spectral characteristics of the interrogated optical sensor 114, but also may depend, to a significant extent on the applied temperature modulation of the laser source 222, and/or the current modulation of the laser source 222. Accordingly, the change in output optical power limits an absolute accuracy of a detected response from the optical sensor 114, and thus the accuracy of the spectral characteristics of the optical sensor 114. Accordingly, in another aspect, the variations in an output power of the laser source 222 may be measured and used to improve an accuracy of the spectral characteristics measurement.

Figure 3:
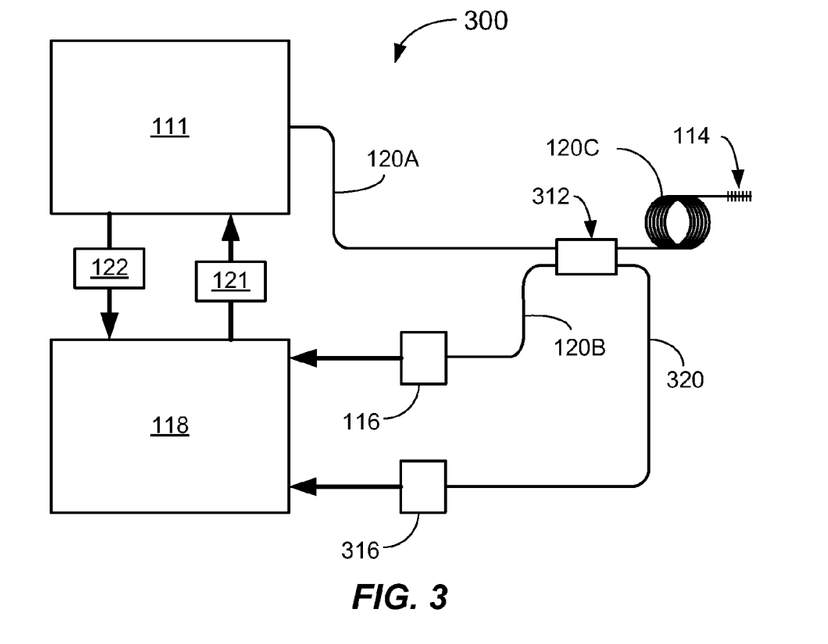
FIG. 3 is a schematic diagram of an opto-electronic signal processing apparatus according to further embodiments of the invention.

In another embodiment of opto-electronic signal processing apparatus 300, as best shown in FIG. 3, an additional light receiver 316 (e.g., a photodetector), of the type described above for light receiver 116, may be added to minimize or eliminate adverse optical power modulation effects of temperature and/or current described above. This may be accomplished by measuring a total optical power emitted by the integrated laser module 111. The opto-electronic signal processing apparatus 300 may include, in this configuration, an optical coupling element 312 including four ports, where the additional port redirects a constant fraction of the optical power emitted by the laser source of the laser module 111 directly to the additional light receiver 316 through a length of optical fiber 320. The optical power intensity measured by the additional light receiver 316 may be used to normalize the power detected by the primary light receiver 116 and, thus, reflected spectral characteristics recorded during a wavelength sweep at the primary light receiver 116 may be normalized to become approximately independent of variations in the output power of the integrated laser module 111.

In an optional configuration, an additional photodetector may be included within the integrated laser module 111 as a third intensity-measuring photodetector provided adjacent to the two intensity-measuring photodetectors 225, for the detection of emitted output power. Part of the light from laser source (e.g., laser diode) in this embodiment may be directed to third photodetector (and not through the etalon) and the other part is directed through the etalon to the pair of photodetectors 225. The third photodetector (not shown) therefore may directly measure laser diode emitted power. In this case, an additional port on the optical coupling element is not necessary. In yet another alternative embodiment, an additional passive optical coupling element may be included between the integrated laser module 111 and the optical coupling element 112 in optical fiber 120A. In this embodiment, one port of such a passive coupling element may be connected directly to an additional photodetector, which then may measure an output power of the integrated laser module 111. This measured value may be used to normalize the optical signals provided from the light receiver 116, such that the effects of power variations on the measured spectral characteristics of the optical sensor 114 may be reduced or eliminated.

In order to extract a measured parameter (e.g., strain, temperature, pressure, acceleration, refraction index, displacement, and others) from measured spectral characteristics of the optical sensor 114, it is important to precisely determine a wavelength of a specific measured feature within spectral characteristics of the optical sensor 114. Such a measured feature may be, for example, peak reflectance wavelength, peak reflectance wavelengths, a wavelength at a maximum slope within the spectral characteristics, or other similar measured feature(s). Therefore, it is desirable that the optical power received by the light receiver 116 be accurately correlated to the emitted wavelength of the integrated laser module 111. While direct correlation of the drive current and/or temperature to the emitted wavelength is possible, such correlation may not provide sufficient accuracy due to a limited ability to precisely determine a temperature of an active region of the laser diode, and also due to the laser diode aging effects. Therefore, the internal wavelength measurement apparatus 223 of the integrated laser module 111 may be used to provide a relatively more accurate correlation between the emitted wavelength and the power received at the light receiver 116. Usually, the wavelength measurement apparatus 223 which is a wavelength locking apparatus is designed to lock the emitted wavelength of the laser diode to specific wavelength (e.g., a specific telecom optical channel). However, in the present invention, the wavelength locker is used to provide an accurate wavelength measuring apparatus.

In the present invention, the wavelength measurement apparatus 223 is used to precisely determine a wavelength of the emitted light within a limited range of the optical spectra of the laser source 222, i.e., an instantaneous wavelength within the wavelength sweep between a first wavelength and a second wavelength.

Figure 4:
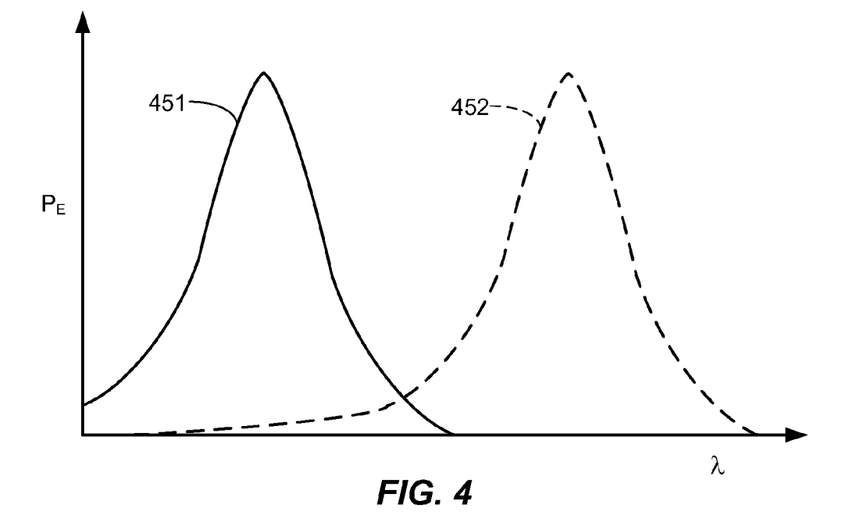
FIG. 4 is an exemplary plot of a spectral response of Power Emitted (PE) as a function of wavelength ($\lambda$) received by photodetectors of a wavelength locker in an integrated laser module.

Referring again to FIG. 2, the integrated laser module 111 may include a wavelength measurement apparatus 223 in the form of a wavelength locker. The wavelength locker may be made from Fabry-Perot etalon and a pair of intensity-measuring photodetectors 225. The Fabry-Perot etalon and intensity-measuring photodetectors 225 may be provided in a spaced geometrical configuration and orientation so that the emitted power (light intensity) $P_E$ from the laser source 222 incident on each of the intensity-measuring photodetectors 225 is almost identical, but may be shifted in wavelength λ based upon a shifted pass band characteristic of the etalon. A wavelength response 451 of a first one of the intensity-measuring photodetectors 225 is, therefore, shifted within a wavelength domain when compared to a spectral response 452 of the second photodetector 225, wherein both responses are shown in FIG. 4.

The wavelength shift between the spectral responses 451, 452 of the intensity-measuring photodetectors 225 may depend mainly on the geometrical configuration of the etalon and positioning the intensity-measuring photodetectors 225. Under the normal operation of the wavelength locker in telecom systems, signals from detectors 451 and 452 would be subtracted to form an error function that is further used in a feedback of a closed loop temperature control of the laser source 222.

However, in order to use the present wavelength locker as a stable, accurate and repeatable wavelength measurement subsystem as in the present invention, it is desirable to further normalize any differences in power between the intensity-measuring photodetectors 225. Normalization may be accomplished by either normalizing by totally emitted power, or normalizing by the sum of the optical powers received by both intensity-measuring photodetectors 225. This desire for normalization arises because a difference in the optical powers received by the intensity-measuring photodetectors 225 depends, in total, upon the laser emitted optical power, except in the case where both received powers are the same (e.g. at a designed or predetermined locking wavelength of the wavelength locker).

Wavelength measurement by a wavelength locker is obtained by calculating the wavelength locker characteristic function w(λ):

$$w(\lambda) = \frac{I_{det1}(\lambda) - I_{det2}(\lambda)}{I_{det1}(\lambda) + I_{det2}(\lambda)}$$

Where w(λ) represents the wavelength locker characteristic function, and $I_{det1}(\lambda)$ and $I_{det2}(\lambda)$ are functions (e.g., functions 451 and 452) of the optical powers incident I on the photodetectors 225.

The wavelength locker characteristic function w(λ) is preferably recorded (calibrated) for the integrated laser module 111 and stored into a memory of electronic control and processing unit 118. This recording may be accomplished by performing a calibration. A calibration may be accomplished with the assistance of an external reference, high resolution spectrum analyzer connected to the integrated laser module 111. For example, a wavelength of the laser source 222 may be slowly increased in wavelength by temperature control via adjusting the thermoelectric cooler 226, while the wavelength locker characteristic function w(λ) is simultaneously recorded together with the spectrum analyzer's readings. The calibration process may be preformed prior to performing a first wavelength measurement according to the invention, i.e., before interrogating an optical sensor 114.

Figure 5:
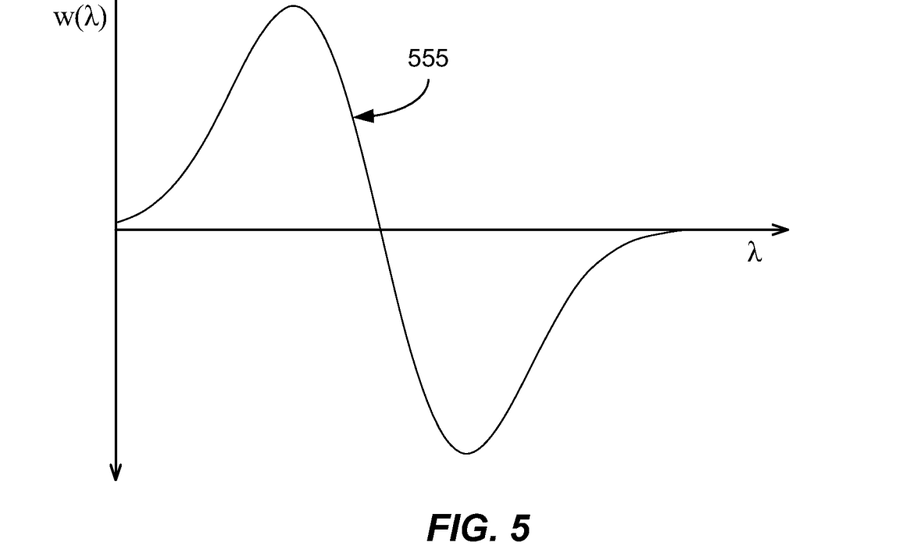
FIG. 5 is a plot of a characteristic function w($\lambda$) of a wavelength locker as a function of wavelength ($\lambda$).

A typical characteristic 555 of a wavelength locker plotting wavelength locker characteristic function w(λ) against wavelength (λ) is presented in FIG. 5. The wavelength locker characteristic function w(λ) may be generally independent of the laser diode output power, as well as a temperature of the laser source 222 of the integrated laser module 111.

Once the calibration has been completed, an operating wavelength (λ) of the operating integrated laser module 111 can be precisely determined. Determination of the operating wavelength of the integrated laser module 111 includes the following steps:

acquisition of optical powers 451 and 452 incident on the detectors 225, calculation of wavelength locker characteristic function w(λ) from the acquired intensity values detectors 451 and 452, and comparison of the calculated parameter w(λ) to the stored function w(λ) of the wavelength locker within memory of the electronic control and processing unit 118 to extract the operating wavelength (λ). The values of the stored function w(λ) of the wavelength locker as a function of wavelength (λ) may be stored in a lookup table, for example. Optionally, the stored function w(λ) may be provided in memory as a mathematical function, spline functions, multiple mathematical functions, or other mathematical formulations.

The usage of integrated laser module 111 to obtain the operating wavelength (λ) of the laser source 222, therefore, may eliminate a need for additional measurements of wavelength or the usage of any additional reference elements to obtain emitted wavelength (λ). Signals generated from the wavelength measuring apparatus 223, such as the wavelength locker, may be directly applicable for determining wavelength with relatively high precision and stability.

It is important to stress that the above-presented method is relatively independent of the emitted laser power, unlike those cases where simpler single wavelength external references are applied. Simple, single wavelength references, as used in prior art systems, can only provide limited accuracy under conditions where source output power changes simultaneously with wavelength.

Operation of the opto-electronic signal processing apparatus 100, 300 heretofore described may, for example, include one or more continuous wavelength sweeps of the laser source 222, from a first lower wavelength ($\lambda_1$) to a second higher wavelength ($\lambda_2$), achieved by temperature control of the integrated laser module 111, controlling a drive current applied to the laser source 222, or a combination of temperature and current modulation. During the wavelength sweeps, the method may further include substantially simultaneous measuring and recording (storing in memory) of the measured intensities of the wavelength locker, and the back-reflected optical power received by the light receiver 116 during such wavelength sweeps. Calculated values of wavelength locker characteristic function $w_c$ are then compared to the stored wavelength locker characteristic function $w(\lambda)$ to obtain an exact wavelength $\lambda$ at which each corresponding recorded reading in time of the light receiver 116 has occurred. Each wavelength sweep, therefore, may result in a recording of spectral characteristics of the optical sensor 114, and determination and a precise recording of the operating wavelength $\lambda$ of the laser source 222 within the wavelength range that corresponds to the wavelength sweep range. Such recorded spectral characteristics of the optical sensor 114 stored in the memory of the electronic control and processing unit 118 may be further processed to extract any desired measured parameter (see above). For example, how an optical sensor 114 reacts under an influence of specific parameter is usually defined by the manufacturer of optical sensor 114. For example, a manufacturer may specify that spectral characteristic of a Bragg grating will shift 1 pm per 1$\mu\epsilon$ (where $\mu\epsilon$ is micro-strain). From the shift in spectral characteristics, strain can be readily determined. For example, if the initial peak is located about at 1272 pm, a shift therefrom may be determined based upon the strain exposed to the optical sensor. For example, once the spectral characteristic of the optical sensor is obtained and stored into the memory of the electronic control and processing unit 118, a peak searching algorithm may be applied to find a maximum or a maxima in the spectral characteristics. In optical sensors, such as Fiber Bragg Gratings, the wavelength corresponding to a maximum reflectivity may be directly correlated to the measured parameter. In optical sensors with periodic spectral characteristics, such as a Fabry-Perot sensor, a position of a certain maximum in the spectral characteristic can be tracked or distance between multiple peaks can be measured to determine the measured parameters. Peak searching algorithms may be realized in many ways, including, but not limited to, simple scanning of all stored values in memory for a maximum value, interpolation of the spectral characteristic with mathematical function (e.g., curve fitting), derivation of this function and solving its derivative for zero, and similar methods. It is however also possible to search for features other than peaks in the spectral characteristic, such as minima, periodic characteristic phase change in a wavelength domain, certain values of characteristic slopes or its derivates, number of peaks and/or minimums within certain wavelength range, or similar features. The spectral features of interest and procedures for their extractions will in generally depend on the construction of the optical sensor and the optical sensor's' general characteristics.

Figure 6:
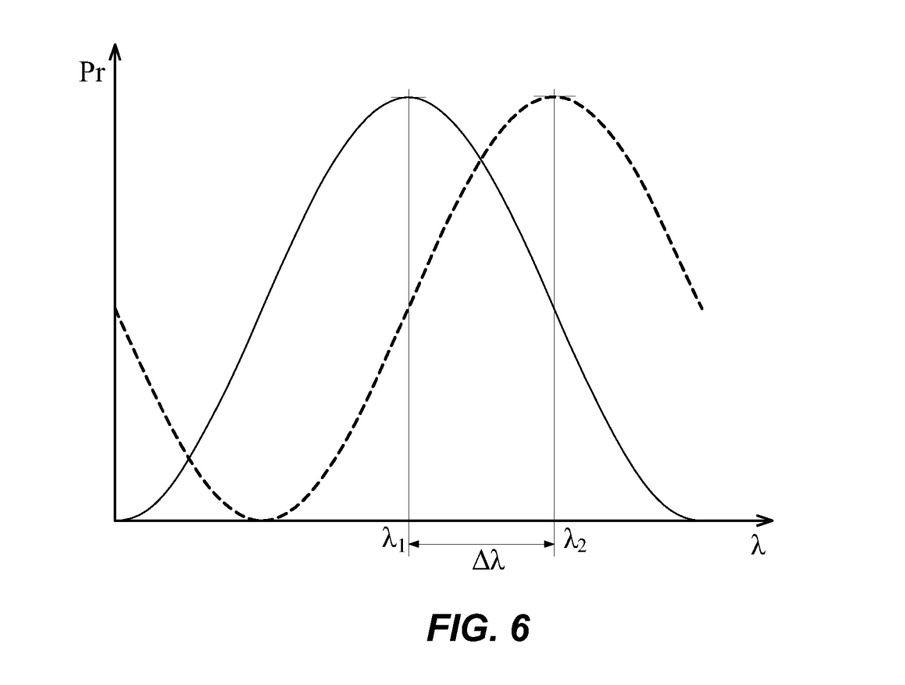
FIG. 6 is a plot of a spectral characteristic of a Fabry-Perot based optical sensor regarding a wavelength shift under an influence of a measured parameter.

As should be understood, different optical sensors 114 may have different spectral characteristics and, therefore, may require different processing of the recorded spectral characteristics of the optical sensor 114 in order to extract a measured parameter therefrom. For example, measurement of a spectral characteristics of a Fabry-Perot interferometer based sensor with low finesse and short distances between mirrors, as presented in FIG. 6, have, for example, an approximately cosine shape. The spectral characteristics may shift (e.g., shift from $\lambda 1$ to $\lambda 2$) within the wavelength domain when the optical sensor 114 is exposed to the measured parameter. The shift (i.e., change in location of a position of a peak reflected power (Pr)) of the spectral characteristic feature, within the wavelength domain, may be proportional to the measured parameter. In other words, $\Delta\lambda$ may be directly proportional to the measured parameter.

Figure 7:
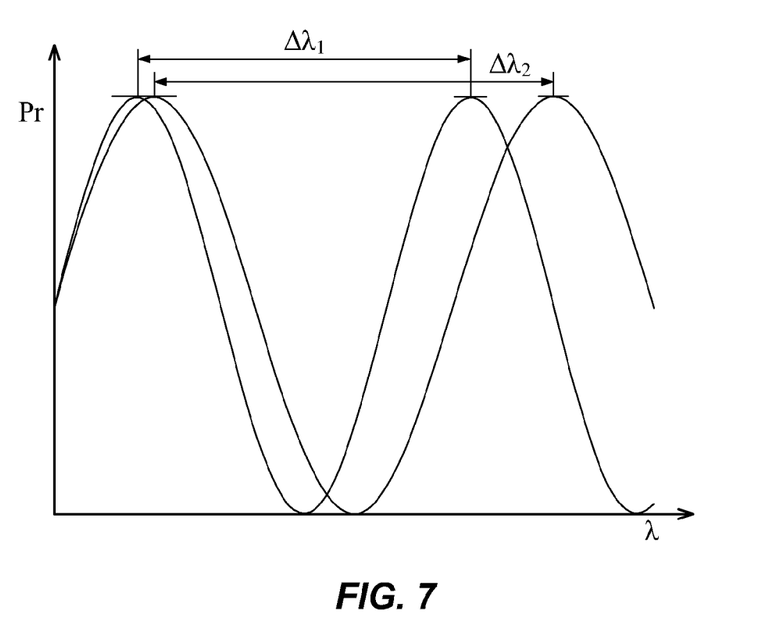
FIG. 7 is a plot of spectral characteristics of a Fabry-Perot based optical sensor, regarding a change in a period thereof under the influence of a measured parameter.
Figure 9:
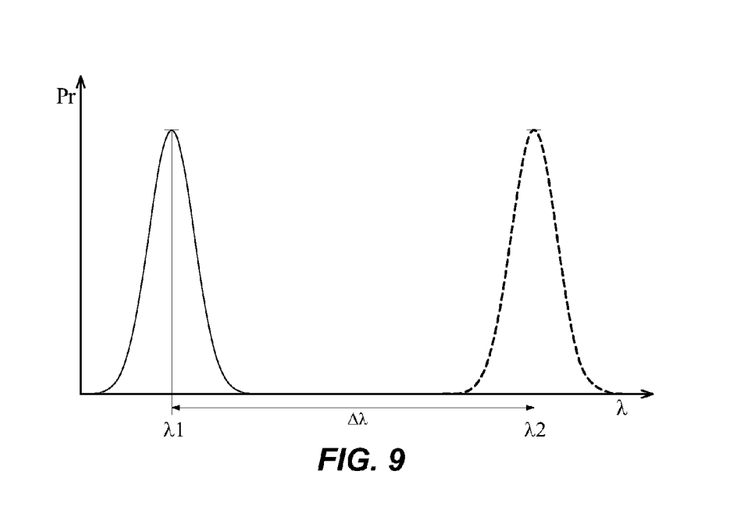
FIG. 9 is a plot of spectral characteristics of a Bragg grating optical sensor, regarding a wavelength shift under an influence of a measured parameter.

A similar response may be observed for a Bragg grating based optical sensor that exhibits spectral characteristics similar to a band pass wavelength filter. These types of grating-based optical sensors may only reflect at narrow and relatively a well-defined band of wavelengths, as presented in FIG. 9. A Bragg grating based optical sensor may shift a peak wavelength shift from $\lambda 1$ to $\lambda 2$ under any change in the measured parameter. In longer all-fiber Fabry-Perot interferometer based sensors, for example, any change in period of their spectral characteristics (e.g., from $\Delta\lambda 1$ to $\Delta\lambda 2$) may be used to obtain a value for the measured parameter, as illustrated in FIG. 7. The change in period may be proportional to the change in measured parameter.

Figure 8:
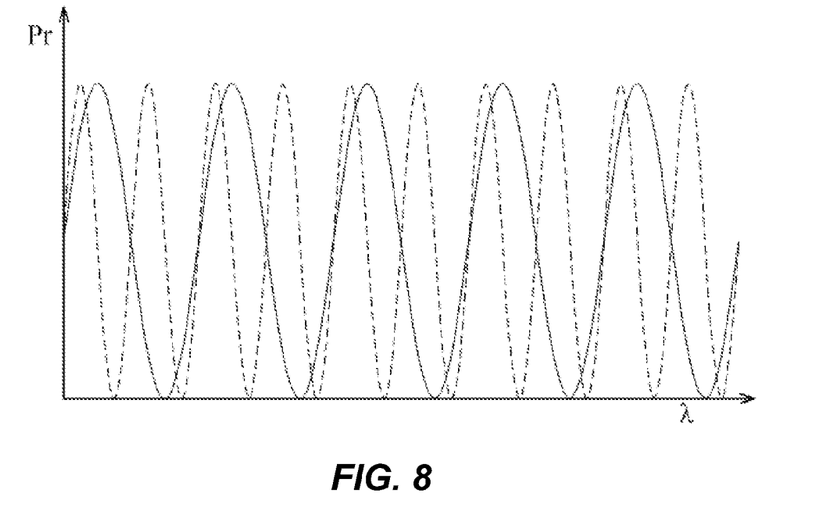
FIG. 8 is a plot of spectral characteristics of a Fabry-Perot based optical sensor, regarding a change in fringe number under an influence of a measured parameter.

In another example, spectral characteristics of a long Fabry-Perot based sensor might have many periods within the observed wavelength range, as presented in FIG. 8. Under the influence of a measured parameter, the periods and position of spectral characteristics (e.g., peaks) may change. The change of the period may be proportional to the change in measured parameter.

Various advanced algorithms can be used to post-process entire, or partially-recorded, sensor spectral characteristics including, but not limited to, approximation with single or multiple mathematical functions using least square or similar approximation methods, filtering algorithms (digital low pass, band pass, etc.), peak searching algorithms (solving first derivative of the approximated function for zero, direct searching for a maximum value in stored lock-up table, etc.) These presented algorithms are only examples of possible algorithms that may be used with the invention.

Figure 10:
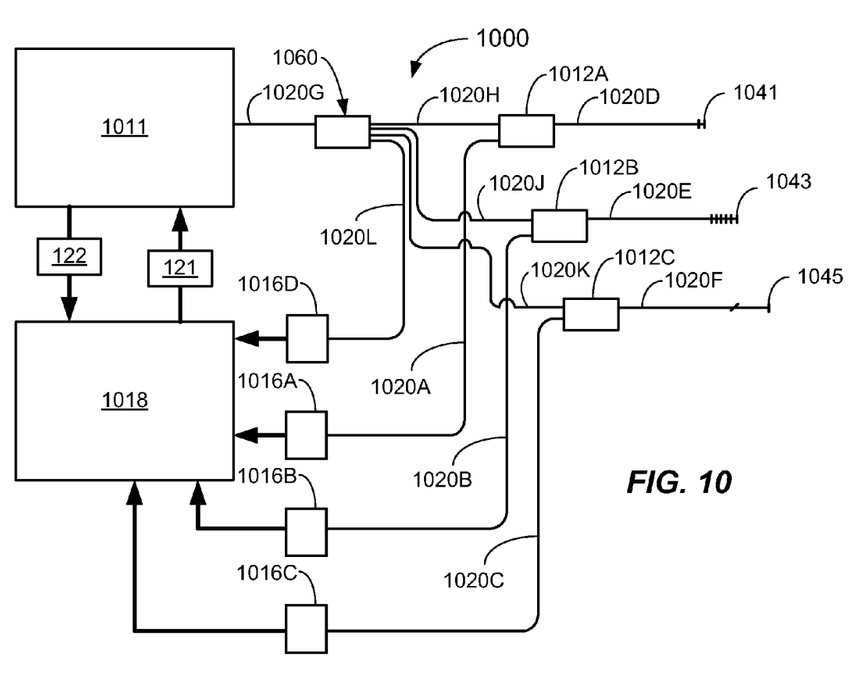
FIG. 10 is a schematic diagram of an opto-electronic signal processing apparatus according to embodiments of the invention, which is adapted for interrogation of multiple optical sensors.

The embodiments presented above may allow for the interrogation of a single optical sensor 114. It is, however, possible to extend the present invention to embodiments that allow for interrogation of more than one optical sensor. FIG. 10, for example, illustrates another opto-electronic signal processing apparatus 1000 according to embodiments of the invention. This embodiment provides multi-channel interrogation and introduces an additional optical coupling element 1060 including N+1 output ports. This configuration allows for interrogation of N sensors (channels) where N represents an integer number. The depicted embodiment shows three connected optical sensors 1041, 1043, 1045. However, it should be understood that two or more optical sensors may be interrogated by the present apparatus 1000.

Each of the N channels may include a passive optical coupling element 1012A-1012C and a light receiver 1016A-1016C (e.g., photodetectors), which are optically connected by suitable lengths of optical fiber 1020A-1020C adapted to receive reflected light signals from each of the optical sensors 1041, 1043, 1045. The optical coupler 1060 may be optically connected to the integrated laser module 1011 by a length of optical fiber 1020G and to respective ones of the optical couplers 1012A-1012C by suitable lengths of optical fiber 1020H, 1020J, 1020K. The plurality of optical sensors 1041, 1043, and 1045 may be connected to respective ones of the passive optical coupling elements 1012A-1012C by respective suitable lengths of optical fiber 1020D-1020F.

In operation, the opto-electronic apparatus 1000 is adapted to interrogate all the optical sensors 1041, 1053, 1045, and may do so simultaneously. The opto-electronic optical apparatus 1000 may allow interrogation of the same type or different types of optical sensors all at once. For example, in the depicted embodiment, the optical sensors may include a short all-fiber Fabry-Perot sensor 1041, the Bragg gratings based sensor 1043, or along all-fiber Fabry-Perot sensor 1045.

As in the previously above-described embodiment, an additional light receiver 1016D (e.g., photodetector) may be optically coupled to an output port of the optical coupling element 1060 by a length of optical fiber 1020L. A signal from the light receiver 1016D may be utilized by the electronic control and processing unit 1018 to enable normalization of the received light signals at light receivers 1016A-1016C to account for power variations resulting from the temperature and/or current modulation of the laser source. Integrated laser module 1011, couplers 1060, 1012A-1012C, optical fibers 1020A-1020H and 1020J-1020L, and light receivers 1016A-1016D in this embodiment may be the same as any of the like components heretofore described. The electronic control and processing unit 1018 may be the same as before described, except that multiple channels of signals may be processed at once thereby.

Figure 11:
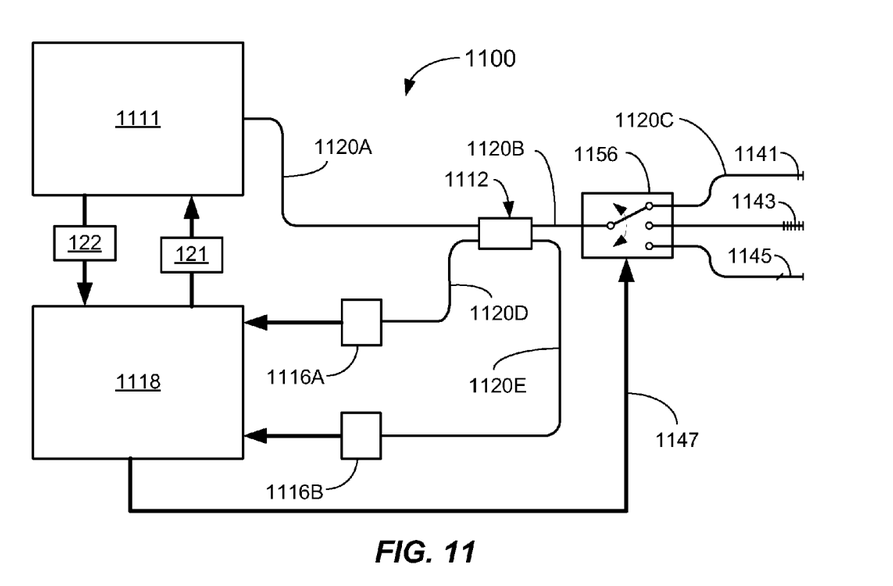
FIG. 11 is a schematic diagram of an opto-electronic signal processing apparatus including an optical switch according to embodiments of the invention for interrogation of multiple optical sensors.

FIG. 11 depicts another embodiment of an opto-electronic signal processing apparatus 1100. This embodiment is similar to the previously described embodiment in that it may interrogate a plurality of optical sensors 1141, 1143, 1145, which may be arranged in parallel. However, in this case, each optical fiber sensor 1141, 1143, 1145 is optically connectable to the integrated laser module 1111 by a multichannel optical switch 1156. This configuration of apparatus 1100 may interrogate each optical sensor 1141, 1143, 1145 individually by switching between the optical sensors under the control of switching signals sent from the electronic control and processing unit 1118 to the multichannel optical switch 1156 in line 1147.

Similar to the previously-described embodiments, in operation, a swept light signal from the integrated laser module 1111 passes through a length of optical fiber 1120A, through optical coupling element 1112 (e.g., an optical coupler) and through a length of optical fiber 1020B. The swept light signal then passes through the multichannel optical switch 1156 and into the optical sensor which the switch 1156, at the moment, is directed towards (e.g., optical sensor 1141). The switch 1156 may be selectively engaged with one of the sensors 1141, 1143, 1145 by moving a switch contact between respective poles of the switch 1156. A length of optical fiber 1020C may optically connect the multichannel optical switch 1156 and the optical sensor 1141, for example. Similar lengths of optical fiber may be used for connecting the other sensors 1143, 1145. Reflected light power from the optical sensor 1141, which is being interrogated, may pass through the optical coupling element 1112 and is diverted by the coupler 1112 to the light receiver 1116A through a length of optical fiber 1020D.

A fraction of the power may pass through optical fiber 1120E to a light receiver 1116B. This signal may be provided to the processing and control unit 1118 to be used as a signal for normalizing the signal received from light receiver 1116A, as described above. This type of apparatus 1100 may have a relatively slower dynamic response than the previous embodiment, but it can interrogate a large number of optical sensors at lower losses of the optical power than the previous embodiment. The multichannel optical switch 1156 may be switched to optically couple to another of the optical sensors 1143, 1145 upon completion of the sweep for optical sensor 1141.

Figure 12:
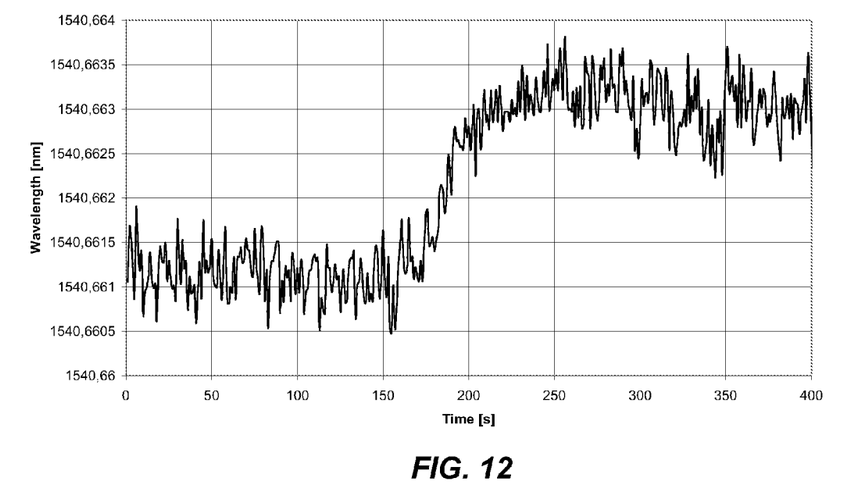
FIG. 12 is a plot of wavelength (nm) versus time(s), which illustrates interrogation of an optical sensor and a measured change in peak wavelength of a low finesse 1 mm long Fabry-Perot temperature sensor, at a change of temperature of 0.2° C.

FIG. 12 illustrates a plot of an example of practical signal integration of an exemplary optical sensor, which is a 1 mm long all-fiber Fabry-Perot sensor. One of the peak wavelengths in the reflected spectral characteristics of the optical sensor was determined and traced by an appropriate algorithm to determine a change upon exposure to a physical parameter. It is apparent based upon the measurement that change of a measured parameter (temperature) of the sensor of about 0.2° C. causes a resultant change in a measured peak wavelength of about 2 pm. From this experiment, it is apparent that the opto-electronic signal processing apparatus, system and method of the present invention may interrogate optical spectral characteristics with at least pico meter resolution.

An apparatus similar to FIG. 3 was used for this test. An approximately 1 mm long FP interferometric optical sensor was inserted into a temperature calibrator which was set to desired temperature (example 30° C.). The system then sweeps to search for a peak wavelength within specific wavelength range of the spectral characteristics. Peak wavelength is than recorded over time and may be presented in a graphical format. After some time, the temperature of the sensor was raised 0.2° C. and a change in a position of the peak wavelength was observed. The change in peak wavelength may then be correlated to the known temperature thereby providing a characteristic function which relates change in peak wavelength to change in temperature to which the optical sensor is exposed. This graph illustrates that it is possible to measure a wavelength dependent feature with high resolution. In this particular case where accuracy of the system is around 0.1° C.

Figure 13:
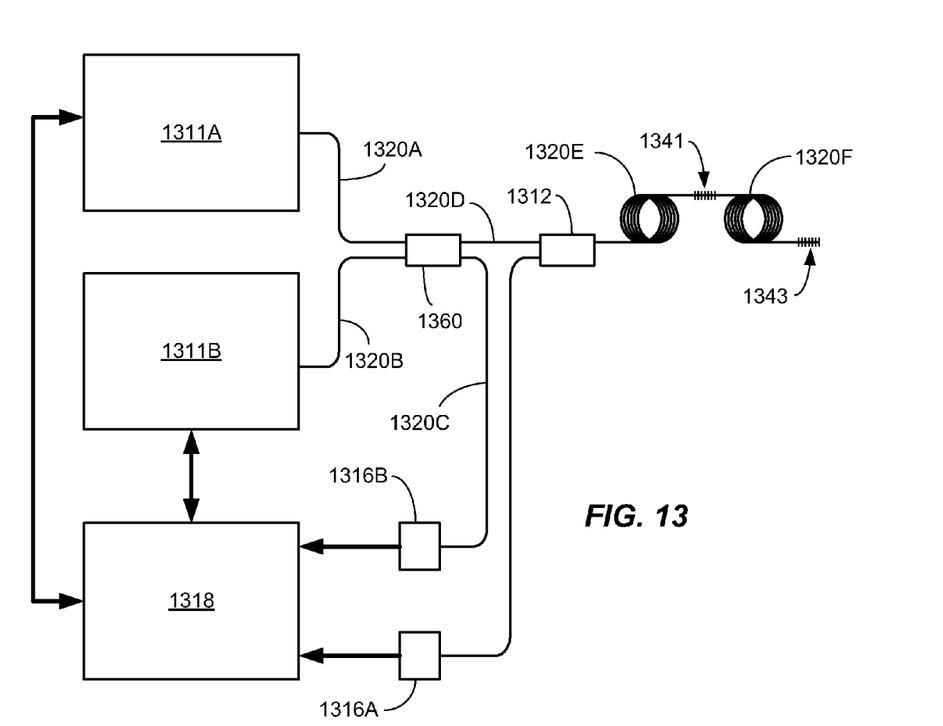
FIG. 13 is a schematic diagram of another opto-electronic signal processing apparatus according to further embodiments of the invention.

FIG. 13 illustrates another embodiment of an opto-electronic signal processing apparatus 1300. This embodiment is similar to the previously described embodiment in that it may interrogate a plurality of optical sensors 1341, 1343. However, in this embodiment, the optical sensors 1341, 1343 are arranged in a series relationship. This arrangement allows for interrogation of multiple optical sensors 1341, 1343 located along the same transmission fiber. In more detail, this embodiment includes a plurality of integrated laser modules 1311A, 1311B of the type described above. Each of the integrated laser modules 1311A, 1311B may have a central emission wavelength $\lambda_c$ substantially matched to the approximate characteristic wavelength of the optical sensors 1341, 1343.

Electronic control and processing unit 1318 may control an emitted wavelength of each of the integrated laser modules 1311A, 1311B by modulating the emitted wavelength by using the temperature dependency and/or drive current, as described above. At substantially the same time, the electronic control and processing unit 1318 may determine the output wavelengths of each of the integrated laser modules 1311A, 1311B by correlating the output signals from the wavelength measurement apparatus integrated within each of the integrated laser modules 1311A, 1311B, as described above. Both of the integrated laser modules 1311A, 1311B may be connected by lengths of transmission optical fiber 1320A, 1320B to an optical coupling element 1360 (e.g., an optical coupler). As before, the output fraction of the power from each of the integrated laser modules 1311A, 1311B may be provided to a light receiver 1316B through length of fiber 1320C, so that the variations in reflected power for each laser may be normalized. The other fraction of the output power from the integrated laser modules 1311A, 1311B is provided through optical fiber 1320D through optical coupling element 1312 and to the string of optical sensors 1341, 1343. Since all the integrated laser modules 1311A, 1311B share the same optical system, they cannot operate simultaneously but must be operated in time sequences. Each optical sensor 1341, 1343 in the string of optical fibers 1320E, 1320F has distinctive spectral characteristics. Each of the integrated laser modules 1311A, 1311B may include an output wavelength selected to match a spectral range of each optical sensor 1341, 1343. For example, integrated laser module 1311A may interrogate optical sensor 1341 and integrated laser module 1311B may interrogate optical sensor 1343. Systems provided in this configuration may be suitable for interrogation of Bragg gratings based sensors. However, the present system may be further combined with other system configurations as described herein to further extend a capacity to interrogated sensors.

Figure 14:
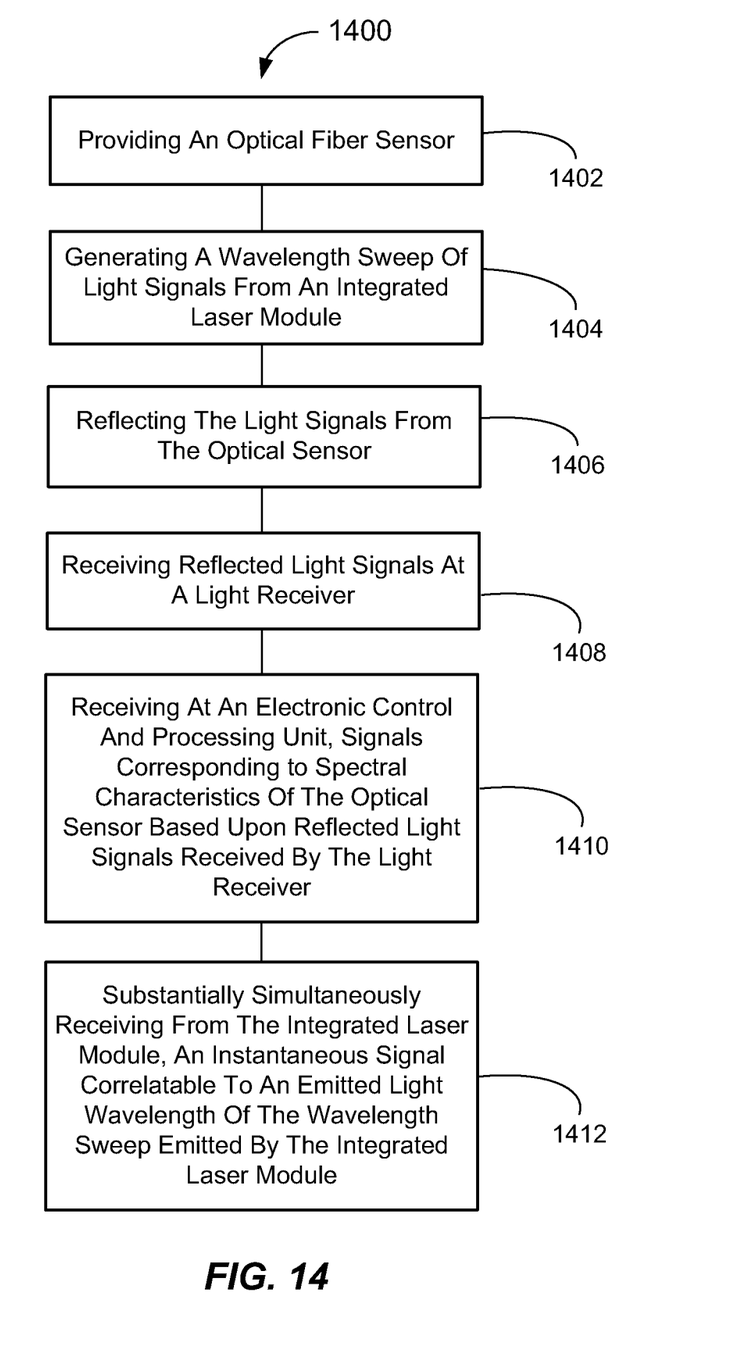
FIG. 14 is a flowchart illustrating methods according to the present invention.

FIG. 14 illustrates a flowchart of a method 1400 of interrogating an optical sensor according to embodiments of the invention. According to the method, an optical sensor to be interrogated is provided in 1402. The optical sensor may be any of optical sensors mentioned above, and may be optically coupled to the opto-electronic signal processing apparatus of the invention as described above. From a laser source of an integrated laser module, a wavelength sweep of emitted light signals (continuous or pulsed) is generated and passed through an optical coupling element to the optical sensor in 1404. The optical coupling element may be any of the coupling elements described above, and may be optically coupled to the integrated laser module and the optical sensor by suitable lengths of optical fiber, for example. Upon reaching the optical sensor, the emitted light signals are reflected from the optical sensor thereby providing reflected light signals in 1406. These reflected light signals are passed through the optical coupling element, diverted and received at a light receiver in 1408. Based upon the reflected light signals received by the light receiver in 1408, signals (e.g., electrical signals) corresponding to spectral characteristics of the optical sensor are sent by the light receiver and are received at an electronic control and processing unit in 1410.

Substantially simultaneously with the receipt of the signals from the light receiver, an instantaneous signal correlatable to an emitted light wavelength of the wavelength sweep being emitted by the integrated laser module is received from the integrated laser module in 1412. Accordingly, reflected intensity values for each optical sensor being interrogated may be relatively exactly correlated with the wavelength for each respective reading. Thus, a precise plot of the spectral characteristics of the optical sensor as a function of wavelength may be determined before and after exposure to a physical parameter. A respective change in a feature (e.g., shift in peak wavelength) of the spectral characteristics of the optical sensor may be correlated to a measured parameter, i.e., a change in the physical parameter. For example, sensitivity of the optical sensor to a change in strain, temperature, pressure, acceleration, refraction index, displacement, and others may be determined.

The following is an example of interrogating an optical sensor in accordance with embodiments of the invention. After the opto-electronic signal processing apparatus is turned on, a temperature of the laser module is stabilized to specific temperature (e.g., 20° C.). After this initial temperature stabilization, current through the thermoelectric cooler is rapidly increased to perform a wavelength sweep of the laser diode to determine the optical sensor's spectral characteristics. The temperature of the laser source is increased by a specified amount (e.g., 10 degrees C.) and at same time, a reflected response of the optical sensor is recorded in memory. An algorithm operating in the electronic control and processing unit then searches for a temperature at which a peak of the sensor's spectral characteristic has occurred. Until this point there was no need for a wavelength measurement.

After the peak temperature (e.g., the temperature at which the peak wavelength of the spectral characteristics is located) is found, the temperature of laser source is set to temperature that is slightly lower than peak temperature (for example 0.5° C. less). Now the scan is repeated around the peak wavelength, so that the peak position may be more precisely identified. After the temperature of laser module is set near the peak, a rapid scan of the optical sensor is provided by using the drive current to the laser source. The drive current may be changed much faster than temperature of the laser source (e.g., laser diode) and is therefore used to improve dynamic properties of interrogation system. Simultaneously with current sweep, a response from the wavelength locker of the integrated laser module is recorded by the electronic control and processing unit, which provides information about the operating wavelength of the laser diode during the sweep.

An algorithm in the electronic control and processing unit then processes the data recorded during the sweep to extract the peak wavelength, which is later converted into a measured parameter. To determine the peak, the recorded normalized sensor back reflected power is approximated with a polynomial function using least square approximation method. The normalized sensor back reflected power is defined as the sensor back reflected power divided by the reference sensor power. Next, a derivative of the normalized sensor back reflected power is obtained and solved for zero (the derivative is simply determined from polynomial function coefficients, which allows direct calculation of approximated function maximum without the need for complex numerical zero searching algorithms). Once the point in swept characteristics that corresponds to the peak reflection is determined, we use the values recorded from the wavelength locker detectors at the same point of the spectral characteristics to calculate actual wavelength of the peak. The wavelength of the peak is obtained by taking a ratio of recorded response at both wavelength locker detectors. This ratio is the set equal to wavelength locker characteristics (that is stored in the unit's memory in form of polynomial spline function) and solved for zero by any numerical method (e.g., using an ordinary tangent and secant method such as by first using a tangent and then secant method to optimize speed and accuracy).

The peak position obtained by the fast current sweep is also used as a feedback for the temperature control of integrated laser module, which is fine adjusted in such way that a position of peak wavelength is always approximately in the middle of current sweep range. This eliminates the need for continuous temperature sweeping of the laser diode, but allows for continuous adjustment of the diode temperature (wavelength sweep range) to the actual value of the measured parameter. The absence of the need for continuous temperature scans increases a potential scanning rate of the opto-electronic signal processing apparatus.

In summary, first an approximate peak position is found with a sweep (based upon temperature dependency of the laser diode) that is relatively slow. Then we use rapid and continuous (non-stop) current sweep to determine an accurate peak position of the spectral characteristics. After each sweep we additionally provide feedback to the temperature control loop that adjusts the temperature in the way that keeps the peak in a middle of the current sweep range and thereby provides tracking of the laser diode temperature with changing measured parameter.

In this example, the wavelength locker data is used to calculate an actual wavelength of the peak. There is no need to correlate the entire recorded spectral characteristics to wavelength in cases where only the peak location is desired to be determined. In the present example, temperature dependency is used to bring the wavelength of the laser diode near the wavelength of the distinctive spectral feature (e.g., peak). Then, a rapid current sweep is used to find and fast track this spectral feature. If measured value of the spectral feature does not experience rapid and large changes (e.g., temperature and static strain measurements) the present method may provide both a high scanning rate and high accuracy/resolution. This is only one example of many possible ways that temperature dependency and current control of an integrated laser module may be used. Other properties of spectral characteristic may be observed and the present method of using temperature dependency and current control to extract the measured parameter from the spectral characteristics of an optical sensor may be used.

The foregoing description discloses only exemplary embodiments of the invention. Modifications of the above-disclosed apparatus and methods which fall within the scope of the invention will be readily apparent to those of ordinary skill in the art. Accordingly, while the present invention has been disclosed in connection with exemplary embodiments thereof, it should be understood that other embodiments may fall within the spirit and scope of the invention, as defined by the following claims.

The invention claimed is:

1. An opto-electronic signal processing apparatus, comprising:
    an integrated laser module including a laser source, a wavelength measurement apparatus, and one or more elements for thermal control of at least the laser source wherein the wavelength measurement apparatus further includes a wavelength selective element and two photodetectors;
    a light receiver;
    an optical coupling element, having at least a first port, a second port and a third port, the first port of the optical coupling element being optically coupled to the integrated laser module, the second port of the optical coupling element being optically coupled to the light receiver, and the third port of the optical coupling element being optically coupleable to an optical sensor to be interrogated; and
an electronic control and processing unit electrically coupled bi-directionally to the integrated laser module wherein the electronic control and processing unit is adapted to receive spectral characteristics of the optical sensor being interrogated based upon a wavelength sweep of emitted light signals sent by the integrated laser module, reflected by the optical sensor and received by the light receiver, and simultaneously receiving from the integrated laser module a wavelength of light being emitted by the integrated laser module.

2. The opto-electronic signal processing apparatus of claim 1, further comprising a wavelength measurement system providing an output wavelength measurement, which is substantially independent of an output optical power of the integrated laser module.

3. The opto-electronic signal processing apparatus of claim 1, wherein the laser source is one selected from a group consisting of a distributed feedback laser diode, distributed back reflector laser diode, a distributed Fabry-Perot laser diode, and vertical-cavity surface-emitting laser (VCSEL) diode.

4. The opto-electronic signal processing apparatus of claim 1, wherein the wavelength sweep of emitted light signals emitted by the integrated laser module is provided by controlling an electrical drive current flowing to the laser source.

5. The opto-electronic signal processing apparatus of claim 1, wherein the wavelength sweep of emitted light signals sent by the integrated laser module is provided by first controlling a temperature of the laser source and then by controlling an electrical drive current flowing to the laser source.

6. The opto-electronic signal processing apparatus of claim 1 comprising an optical switch with multiple channels switchable in operation to connect the optical coupling element to one of a plurality of optical sensors.

7. The opto-electronic signal processing apparatus of claim 1, wherein the wavelength sweep of emitted light signals emitted by the integrated laser module is provided by controlling a temperature of the laser source.

8. The opto-electronic signal processing apparatus of claim 7, wherein the wavelength sweep of emitted light signals emitted by the integrated laser module is between about 0.8 nm and 4 nm.

9. An opto-electronic signal processing apparatus, comprising:
    an integrated laser module;
    a light receiver;
    an optical coupling element, having at least a first port, a second port and a third port, the first port of the optical coupling element being optically coupled to the integrated laser module, the second port of the optical coupling element being optically coupled to the light receiver, and the third port of the optical coupling element being optically coupleable to an optical sensor to be interrogated; and
    an electronic control and processing unit electrically coupled bi-directionally to the integrated laser module wherein the electronic control and processing unit is adapted to receive spectral characteristics of the optical sensor being interrogated based upon a wavelength sweep of emitted light signals sent by the integrated laser module, reflected by the optical sensor and received by the light receiver, and simultaneously receiving from the integrated laser module a wavelength of light being emitted by the integrated laser module, wherein the integrated laser module is a module designed to emit light with a constant wavelength, within dense wavelength division multiplexing (DWDM) telecommunication systems.

10. The opto-electronic signal processing apparatus of claim 9, wherein the integrated laser module further includes a laser source, a wavelength measurement apparatus, and one or more elements for thermal control of at least the laser source.

11. The opto-electronic signal processing apparatus of claim 9, further including a normalization light receiver adapted to detect an optical power emitted by the integrated laser module.

12. The opto-electronic signal processing apparatus of claim 11 wherein the normalization light receiver is:
    coupled to an output port of the optical coupling element;
    integrated into the integrated laser module; or
    connected through a passive optical coupling element installed between the laser source and the optical coupling element.

13. An opto-electronic signal processing system, comprising:
    an integrated laser module including a laser source, a wavelength measurement apparatus, and one or more elements for thermal control of at least the laser source wherein the wavelength measurement apparatus further includes a wavelength selective element and two photodetectors;

a light receiver;

an optical coupling element being optically coupled to the integrated laser module and optically coupled to an optical sensor to be interrogated; and an electronic control and processing unit electrically coupled bi-directionally to the integrated laser module wherein the electronic control and processing unit is adapted to receive spectral characteristics of the optical sensor based upon a wavelength sweep of emitted light signals sent by the integrated laser module, which are reflected by the optical sensor and received by the light receiver, and simultaneously receive a wavelength of emitted light from the integrated laser module.

14. A method of interrogating an optical sensor, comprising:

providing an optical sensor to be interrogated;

generating a wavelength sweep of emitted light signals from a laser source of an integrated laser module through an optical coupling element to the optical sensor;

reflecting the emitted light signals from the optical sensor thereby providing reflected light signals;

passing the reflected light signals through the optical coupling element and receiving the reflected light signals at a light receiver;

receiving at an electronic control and processing unit, signals corresponding to spectral characteristics of the optical sensor based upon the reflected light signals received by the light receiver; and substantially simultaneously receiving from the integrated laser module, an instantaneous signal correlatable to an emitted light wavelength of the wavelength sweep being emitted by the integrated laser module wherein the emitted light wavelength is determined by:

subtracting an optical power incident on each of two spaced, intensity-measuring photodetectors in the integrated laser module to obtain a difference between the optical powers incident on the two spaced, intensity-measuring photodetectors;

dividing the difference by a sum of the optical power incident on each of the two, spaced intensity-measuring photodetectors in order to obtain a wavelength parameter that is independent of the laser module's output power; and correlating the wavelength parameter with a correlator in memory of the electronic control and processing unit to determine an emitted wavelength of the laser source.

15. The method of claim 14 wherein the correlator is provided in the form of one selected from the group of:

a look-up table;

a mathematical function or formulation;

a spline function; and multiple mathematical functions.

16. The method of claim 14 comprising controlling the wavelength sweep of emitted light signals by controlling, with the electronic control and processing unit an electrical drive current flowing to the laser source.

17. The method of claim 14 comprising controlling the wavelength sweep of emitted light signals by controlling, with the electronic control and processing unit, a temperature of the laser source.

18. The method of claim 14 extracting with the electronic control and processing unit, a measured parameter from a specific spectral feature in the spectral characteristics.

19. The method of claim 18 wherein the specific spectral feature is at least one of:

a peak wavelength in the spectral characteristic;

a distance between two or more peak wavelengths in the spectral characteristic; and a wavelength of occurrence of a maximum slope in the spectral characteristic.

20. The method of claim 18 wherein the specific spectral feature of the spectral characteristics is selected from a group of:

a free spectral range of an interferometric sensor;

a number of periods within a predetermined wavelength range of the spectral characteristic; and a total phase of a sinusoidal spectral characteristic within a predetermined wavelength range.

21. A method of interrogating an optical sensor, comprising:

providing an optical sensor to be interrogated;

generating a wavelength sweep of emitted light signals from a laser source of an integrated laser module through an optical coupling element to the optical sensor;

reflecting the emitted light signals from the optical sensor thereby providing reflected light signals;

passing the reflected light signals through the optical coupling element and receiving the reflected light signals at a light receiver;

receiving at an electronic control and processing unit, signals corresponding to spectral characteristics of the optical sensor based upon the reflected light signals received by the light receiver; and substantially simultaneously receiving from the integrated laser module, an instantaneous signal correlatable to an emitted light wavelength of the wavelength sweep being emitted by the integrated laser module wherein the integrated laser module is designed to provide light with constant wavelength but can be tuned to operate at more than one discreet channel within dense wavelength division multiplexing (DWDM) telecommunication systems.

* * * * *